United States Patent [19]

Rehberger

[11] Patent Number: 5,945,333

[45] Date of Patent: Aug. 31, 1999

[54] BIOLOGICAL POULTRY LITTER TREATMENT COMPOSITION AND ITS USE

[75] Inventor: Thomas G. Rehberger, Wauwatosa, Wis.

[73] Assignee: Ag Tech Products, Inc., Waukesha, Wis.

[21] Appl. No.: 08/918,371

[22] Filed: Aug. 26, 1997

[51] Int. Cl.[6] .................................................. C07G 15/00
[52] U.S. Cl. .................. 435/268; 435/252.5; 435/252.9; 119/171; 119/173
[58] Field of Search ..................................... 435/262, 268, 435/252.4, 252.5, 252.9; 119/171, 172, 173, 174

[56] References Cited

U.S. PATENT DOCUMENTS

| | | | |
|---|---|---|---|
| 5,054,434 | 10/1991 | Wax et al. | 119/171 |
| 5,154,594 | 10/1992 | Gamien | 119/171 |
| 5,507,250 | 4/1996 | Reddy et al. | 119/173 |
| 5,707,856 | 1/1998 | Higa | 435/268 |

OTHER PUBLICATIONS

Hulet, "Poultry Litter Amendments Showing Beneficial Effects", *Poultry Digest*, pp. 12 and 14, Jun., 1997.
Mallinson et al., "Litter Management is Critical to Food Safety, Performance", *Feedstuffs*, pp. 47–49 and 54, May 19, 1997.
Malone et al., "Ammonia Control in the Broiler House--Products and Procedures", *Proceedings to the DeMarva Broiler Housing & Flock Supervisors' Conference*, pp. 22–35, Sep. 18, 1996.

*Primary Examiner*—David A. Redding
*Attorney, Agent, or Firm*—Andrus, Sceales, Starke & Sawall

[57] ABSTRACT

The present invention is a biological waste treatment product that utilizes the activity of scientifically selected bacteria to control the decomposition of poultry litter thereby improving litter quality. The end result is improved health and performance of the birds while also reducing the incidence of foot scabs and other lesions caused by poor litter conditions. Application of the unique combination of bacteria of the present invention results in several biochemical effects proving to be beneficial to the quality of the litter and thus the health and performance of the birds. Specially, bacteria of the present invention produce broad spectrum antimicrobial proteins active against gram (–) bacteria. The reduction of gram (–) bacteria reduces the level of microbial pathogens in the litter as well as reduces the population of gram (–) bacteria that break down uric acid into ammonia. In addition, bacteria in the present invention utilize uric acid as a substrate thus inhibiting the reduction of uric acid to ammonia. Further, bacteria of the present invention produce proteolytic enzymes which break down the protein excretion products from birds which improves the litter quality by reducing the water holding capacity of the litter. Finally, bacteria of the present invention also produce organic acids from starch fermentation which reduces the litter pH and thereby decreases the pathogenic and urilytic bacteria in the litter.

25 Claims, 3 Drawing Sheets

BIOLOGICAL POULTRY LITTER TREATMENT COMPOSITION AND ITS USE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Controlling the condition of litter in poultry houses is essential to ensure a better environment and thus better health and performance of the birds. The condition or quality of litter can be affected by a number of factors such as moisture, temperature, pH, ventilation, stocking density and frequency of cleanout. Of these factors, cleaning out the built-up litter more frequently is the most effective way to control and immediately improve litter quality. Unfortunately, this method of improving litter quality is becoming less of an option for producers since litter costs have dramatically increased in recent years. Therefore, many producers have adopted the practice of reusing litter as a strategy to reduce costs. In broiler houses, litter will routinely be reused for four or more sequential flocks of birds. In turkey grow or finish houses, litter will be reused for two or more sequential flocks of birds. While the reuse of litter has reduced the immediate litter costs, the use of built-up litter necessitates implementing better management practices to maintain litter quality. Poor litter conditions lead to an increase in the populations of microbial pathogens in the litter and excessive ammonia production.

Ammonia is a noxious gas that is produced by the microbial decomposition of nitrogenous waste in the litter. The deleterious effects of ammonia on broiler performance, health and carcass quality have been well documented. The presence of ammonia is a major physiological stress agent which is directly related to the health of the bird. This results in lower weight gain and generally unhealthy birds. Mortality also increases. Prolonged ammonia exposure at concentrations higher than 25 ppm has been shown to denude the cillia of the trachea and leave the bird vulnerable to challenges from respiratory ailments common in commercial poultry houses. High concentrations of ammonia can also blind young chicks.

The ammonia present in broiler and other poultry housing facilities is the product of microbial decomposition of excreted nitrogenous compounds. These compounds consist primarily of uric acid and nonabsorbed proteins, amino acids, and nonprotein nitrogen present in the diet. Approximately 50% of nitrogen excreted by poultry is in the form of uric acid. The nitrogen is derived from the degradation of amino acids which are in excess of metabolic needs for protein synthesis. The carbon that remains is used for (1) glucose synthesis, (2) conversion into fat or (3) metabolized into energy, $CO_2$ and $H_2O$. The remaining nitrogen is excreted in fecal matter.

While all of this excreted nitrogen is readily biodegradable, uric acid is the most rapidly degraded component, with $NH_3$ and $CO_2$ as hydrolysis end products. The enzyme uricase, which can be synthesized by many species of microorganisms, especially gram (−) bacteria, is responsible for this transformation. Given the large and diverse population of microorganisms in broiler litter, uric acid hydrolysis begins almost immediately following excretion. Protein and amino acid degradation, with $NH_3$ as one end product, proceeds at a slower rate due to the greater complexity of these molecules.

Normally, uric acid is converted to allantoin by the enzyme uricase produced by gram (−) bacteria. See Equation 1.

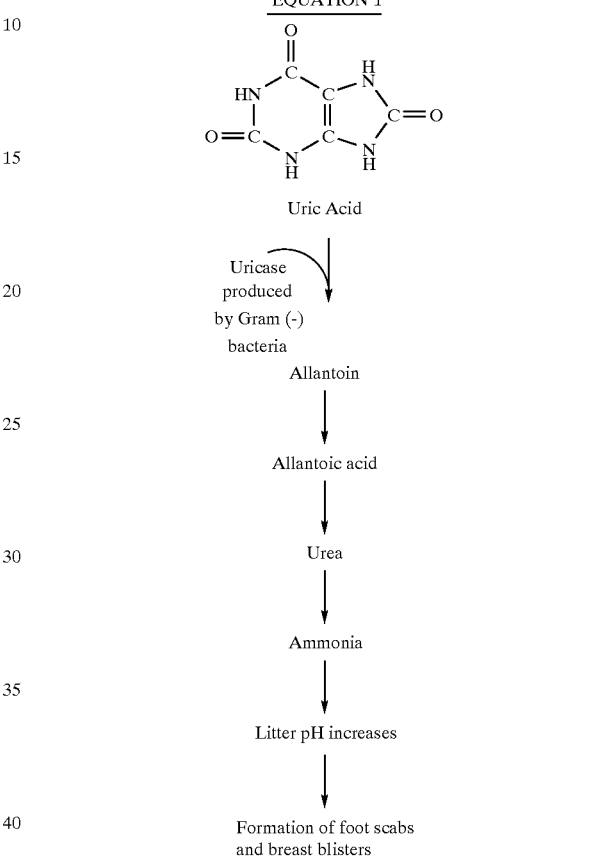

The allantoin is subsequently converted to allantoic acid, then to urea. Finally, the urea is converted to ammonia which results in an increased pH, creating an environment ideal for the formation of foot scabs and breast blisters.

In addition to ammonia, the proliferation of pathogenic microorganism is also a major problem. Caked and damp litter lead to increased pathogenic microbial growth further inhibiting performance of the birds and resulting in a human food safety risk. Spilled feed further compounds the problem since spilled feed and moisture lead to rapid proliferation of these microorganisms. A further problem is caused by excess water accumulating on the litter surface and increasing moisture content. This environment results in a high pathogenic microbial population in the litter.

Research has shown the damaging effects of pathogenic microorganisms on broiler feed conversion and growth. The greater the concentration of pathogens in the house, the greater the decrease in feed conversion and decrease in body weight gain. Since feed conversion and weight gain are significant portions of production efficiency, many growers that are trying to conserve costs by reusing litter are exacerbating the problem resulting in an even greater build-up of pathogenic microorganisms and higher losses.

The emerging market for broiler feet has recently focused attention on problems affecting poultry feet production and quality. One of the major defects reducing the economic value of feet are lesions or what are commonly called "foot scabs".

In addition to foot scabs, many birds also develop "breast blisters" or lesions on the breast. The widespread formation of breast blisters has a potentially devastating impact on the consumer poultry industry.

A number of environmental factors such as temperature, relative humidity and poor ventilation as well as nutritional factors, such as a biotin deficiency and excess salt levels in the diet, have been reported to affect the incidence of foot scabs and breast blisters. The result of the aforementioned environmental factors is wet, caked litter. These poor litter conditions lead to excess ammonia production and increased litter pH, which has now been found to play a primary role in the incidence of foot scabs and breast blisters.

Few treatments to improve litter quality have been reported. The prior art suggests utilizing acidifying compounds or absorbants in order to maintain proper litter pH, reduce ammonia and reduce the microbial load of the litter. However, due to the magnitude and diversity of microbial population in broiler litter and the continual introduction of new organisms in freshly excreted manure and from a variety of other sources, this approach is not always successful.

Further, disinfectants have been used by some in order to dilute the litter and maintain a proper pH. However, maintaining a lethal concentration of disinfectant is critical to its efficacy and to be truly effective, litter would have to be saturated with the disinfecting agent and thoroughly mixed to insure exposure to a lethal concentration of the disinfectant at a frequent interval. What normally results is merely surface applications which only temporarily slows microbial growth.

Others have attempted use of acidifying agents, such as phosphoric acid, aluminum sulfate (alum) or ferrous sulfate to reduce litter pH and thus the concentration of unionized or free ammonia. There are significant variations in effectiveness of this method. Much of this variation is due to the alkalinity or acid neutralizing capacity of litter which increases with litter age. As fecal material accumulates, salts of weak organic and inorganic acids and ammonia, which contribute to litter alkalinity, also increase. Thus, acidifying litter to a pH of 7.0, which is the point where essentially all litter ammonia is in the ionized form, only temporarily reduces ammonia volatilization.

Absorbants, such as clays, function primarily by providing negatively charged exchange sites to attract ammonium ions. In this process, more weakly bound ions such as hydrogen and sodium are replaced by ammonium ions, reducing the total concentration of ammonia in solution. The effectiveness of this ion exchange process in broiler litter is limited by several factors. One is the preference by most materials with ion exchange sites for ions with higher charges, such as calcium, magnesium and phosphorus. Since these ions are present in significant concentrations in broiler manure, absorbent effectiveness per unit volume in reducing ammonia volatilization is reduced and must be compensated for by higher application rates. The second factor is the need for contact between the ammonium ions in solution and the absorbent. Without thorough mixing, the effectiveness of any absorbent is minimal at best.

A primary method growers use for controlling ammonia levels is a properly designed housing structure complete with a ventilation system. Key components of the ventilation system are proper inlet location, air direction, air speed and volume of air. However, older facilities which do not have modern designs or sophisticated ventilation systems are looking at substantial expenses in order to remedy the situation. Also, the energy requirements to maintain a ventilation system are quite high. Further, higher levels of ventilation which lead to lower temperatures are not always tolerated well by growing chicks.

Various chemical treatments have also been described in the prior art but require constant addition to the litter and are quite expensive. Further, these chemical treatments are only able to reduce pH for very short periods of time.

The present inventors have been examining biological treatments for litter to reduce the incidence of foot scabs, breast lesions and illnesses caused by poor litter conditions. Based on extensive laboratory work and field trials, a reliable and cost effective biological litter treatment product has finally been developed. This invention acts as an effective component of a litter management program to reduce production losses due to poor litter quality.

BRIEF SUMMARY OF THE INVENTION

The treatment composition of the present invention consists of a unique combination of bacteria, specifically bacteriocin-producing bacteria, protease-producing bacteria and bacteria capable of fermenting starch into organic acids. The biochemical effects of this invention significantly improves litter quality thereby improving bird health and performance while also reducing the incidence of foot scabs and other lesions caused by poor litter conditions.

Preferably, the unique combination of bacteria consists of Bacillus, *Propionibacterium jensenii*, and *Lactobacillus curvatus*. This bacterial combination has a multi-faceted mode of action to reduce ammonia and pH as well as control pathogens in poultry litter. First, the uric acid excreted by poultry, which is normally converted to allantoin by uricase produced by gram (−) bacteria, is inhibited. Instead, the uric acid is used by the bacteria contained in the novel composition as a nutrient which stops the conversion of uric acid to allantoin.

Second, production of acids from starch fermentation reduces the pH and, therefore, the litter pH on the whole decreases. This decrease in pH leads to a decrease in gram (−) bacteria. The reduction of these gram (−) bacteria is due to a change in pH caused by acidic conditions which disrupt the cellular processes at the molecular level. For example, vital biochemical processes involving ATP are disrupted.

Third, this novel composition prevents continued growth of salmonella, coliform, and other gram (−) pathogenic microbes. The mechanism for this inhibition is via a small molecular weight protein produced by the *Propionibacterium jensenii* which has been shown to inhibit the growth of many gram (−) bacteria. Specifically, these proteins produced by the *Propionibacterium jensenii* are bacterioncins.

DETAILED DESCRIPTION OF THE INVENTION

Figure 1:
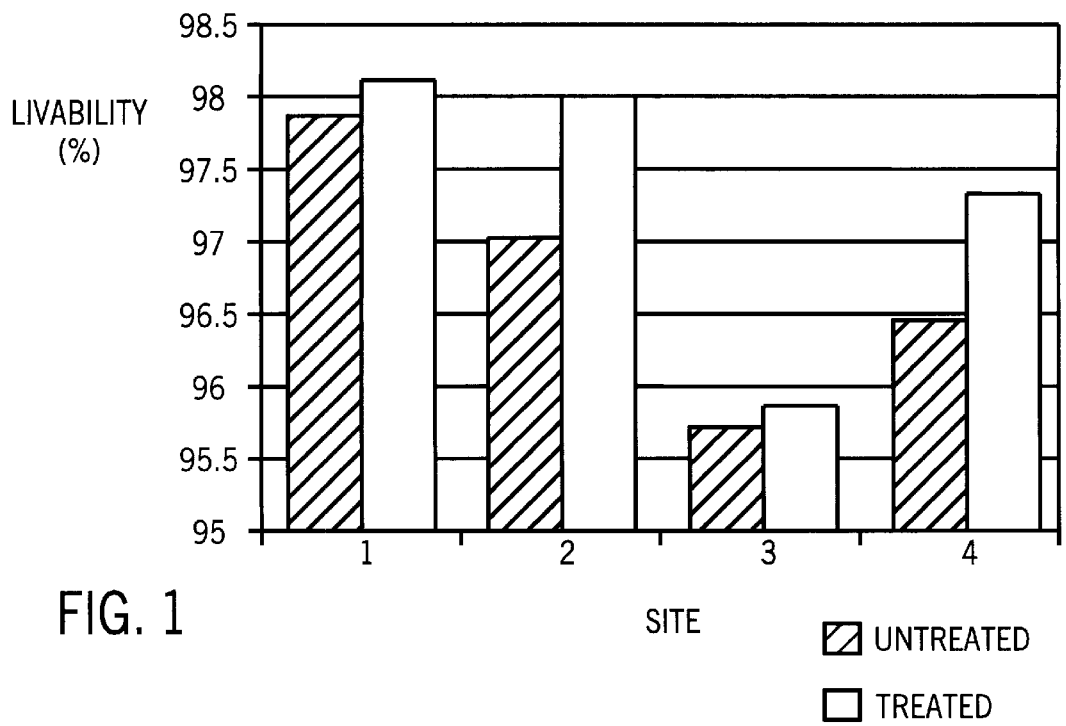
FIG. 1 illustrates the improved livability of birds residing in houses treated with the novel composition.

The unique combination of bacteria in the present invention significantly reduce gram (−) bacteria and ammonia concentrations in poultry litter. The litter of chickens, turkeys, ducks, geese and the like can all benefit from the use of this novel bacterial composition. The bacterial species utilized in this invention include Bacillus, *Propionibacterium jensenii*, and *Lactobacillus curvatus*. Preferably, three strains of Bacillus and Propionibacterium jensenii, strain P63 are preferred. The three strains of Bacillus include *Bacillus licheniformis, Bacillus subtilis* and *Bacillus amyloliquefaciens*. However, any protease-producing bacteria will do, especially those which produce neutral and alkaline proteolytic enzymes.

This unique combination of bacteria results in several biochemical effects proving to be beneficial to the quality of the litter and, therefore, the health of the birds. *Propionibacterium jensenii* strain P63 produces an antimicrobial protein that is active against a broad spectrum of gram (−) microorganisms. As mentioned, these broad spectrum antimicrobial proteins are called bacteriocins. This protein inhibits the growth of gram (−) bacteria. The bacteriostatic inhibition of the gram (−) bacteria in poultry litter is important for two reasons. The first is that many gram (−) bacteria are pathogenic to the birds as well as humans and, therefore, inhibit performance of the birds and pose a human food safety risk.

The second reason inhibition of gram (−) bacteria is important is that gram (−) bacteria are responsible in the decomposition of uric acid. Uric acid is the major nitrogen excretion product of birds and is biochemically broken down into ammonia. At high levels, the ammonia produced by the decomposition of uric acid inhibits the performance of the birds and causes a myriad of problems, as detailed above. Therefore, the inhibition of the gram (−) bacteria reduces ammonia in the poultry houses.

While strain P63 is preferred, any bacteriocin-producing bacteria effective against gram (−) bacteria is contemplated within the scope of the invention, including but not limited to: *Propionibacterium jensenii* strains P9 and P88; *Propionibacterium freudenreichii* strains P93, P99 and P101; and *Propionibacterium acidipropionici* strain P42.

The *Lactobacillus curvatus* species is capable of fermenting starch to produce organic acids. The function of this bacterial strain in the litter is to ferment the available starch in the litter derived from spilled feed. The final result of this fermentation is organic acid production. The organic acids reduce the pH of the litter which thereby inhibits further microbial growth and thus the decomposition of the uric acid and the resulting ammonia. Specifically, the Lactobacillus hydrolyzes the starch via amylases. Amylases hydrolyze the internal $\alpha$-1, 4 linkages in starch to yield maltose, maltotriose and $\alpha$-dextrin. These enzymes further continue to break down these molecules into glucose which in turn enters the Embden-Meyerhof-Parnas pathway where lactic acid is produced.

Any microbe capable of fermenting starch to organic acids, such as lactic acid, are contemplated within the scope of this invention such as *Lactobacillus amylovorus* and *Pediococcus dextrinicus*.

The lower pH in localized areas where organic acids are produced will also inhibit pathogenic bacteria. The limiting factors for the function of *Lactobacillus curvatus* are the availability of starch, i.e. spilled feed, and moisture necessary for the fermentation. These conditions are commonly found along the water lines in the poultry houses. Without the presence of this bacteria species, the spilled feed and available moisture would lead to a rapid proliferation of pathogenic microorganisms.

The third bacterial component of this invention is *Bacillus*. The two key characteristics of the Bacillus strains are to produce extracellular proteolytic enzymes and the ability to utilize uric acid as a nitrogen source. Any Bacillus species is acceptable as long as it is capable of these two functions.

The production of the proteolytic enzymes will aid in the decomposition of protein excretion products from the birds, which is the other type of nitrogen excretion from fowl. The protein excretion products result in caking or sticky litter conditions. The caked and sticky litter is a complex of excreted proteins and tiny particles that agglomerate and then bind or hold water. As the caking increases, the moisture produced by the birds and the water from leaks in water lines accumulates on the surface of the litter and leads to exceedingly high moisture. This in turn results in high microbial populations in the litter including pathogenic bacteria and organisms responsible for decomposition of uric acid to ammonia, thereby compounding the ammonia problem. However, the extracellular proteases produced by *Bacillus* break down the protein excretion products decreasing the caking and sticky litter conditions. This decreases the moisture on the surface of the litter resulting in lower numbers of microorganisms in the litter and a healthier environment for the birds.

The other function of the Bacillus is utilization of uric acid as a nutrient for microbial growth. Thus, Bacillus effectively competes against gram (−) bacteria for uric acid in the litter, thereby reducing the amount of uric acid that can potentially be broken down into ammonia.

The ATCC numbers for the aforementioned bacteria are as follows: *Bacillus subtilis*, ATCC 27505; *Bacillus amyloliquefaciens*, ATCC 23842; *Bacillus licheniformis*, ATCC 21415. The *Propionibacterium jensenii*, strain P63 is deposited in the culture collection at Agtech Products under the strain number P63. The strain is also deposited in the culture collection at Iowa State University under the strain number P63. Originally this strain was received from the Center for Disease Control in Atlanta, Ga. as strain PJ54.

The composition of the present invention preferably contains a carrier, and, in the preferred embodiment, the carrier is water soluble. The primary function of the water soluble carrier is to allow easy dissolving upon contact with a liquid. Suitable water soluble carriers include whey and maltodextrin, such as maltodextrin M100. The water soluble carrier may consist of maltodextrin and whey in approximately a 50/50% ratio. However, any water soluble carrier is suitable within the scope of this invention.

Further, a moisture binding agent is also preferably used. This aids in the prevention of clumping, thereby making the composition easier to use and providing for better handling capabilities. An agent such as balith may be used.

The steps for the production of the bacterial strains of the present invention are fermentation of the bacterial strains, harvesting and freeze drying the cells and milling the freeze dried culture to a uniform size and specified activity. The fermentation is started by scaling-up a seed culture. This involves repeatedly and aseptically transferring the culture to a larger and larger volume to serve as the inoculum for the fermentation. The fermentation is carried out in large stainless steel fermentors in medium containing proteins, carbohydrates and minerals necessary for optimal growth. After the inoculum is added to the fermentation vessel, the temperature and agitation are controlled to allow maximum growth. Once the culture reaches a maximum population density the culture is harvested by separating the cells from the fermentation medium. This is commonly done by centrifugation. The wet cell paste is then mixed with cryoprotectants which will maintain the viability of the cells during the freezing and drying process. The mixture is then placed in trays, frozen and subsequently dried. The resulting dried cake is milled to a uniform size and plated to determine the activity. After the viable cell count has been determined, the cell count is standardized to a predetermined activity level or colony forming units per gram by blending with dry carriers.

The count of the bacteria is important when combined with a carrier. At the time of manufacture of the novel composition, the Bacillus count should be at least $1.17 \times 10^{10}$ CFU/g. The count for the *Propionibacterium jensenii* strain P63 should be at least $6.67 \times 10^9$ CFU/g and the *Lactobacillus curvatus* at $1.66 \times 10^9$ CFU/g. The counts may be increased from these base numbers and still have complete efficacy. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is more correct than cell number.

The aforementioned cultures and the carrier are added to a ribbon or paddle mixer and mixed preferably for 15 minutes. The components must be blended enough so that uniform mixture of the carrier and cultures result. The final product is a dry flowable powder.

The preferred carrier in this composition is created by combining approximately 50% whey, 49% maltodextrin M100 and 1% balith with the freeze-dried cultures of Bacillus, *Lactobacillus curvatus* and *Propionibacterium jensenii*, preferably strain P63. The Bacillus preferably utilized are *Bacillus licheniformis, Bacillus subtilis* and *Bacillus amyloliquefaciens*.

The novel composition used in the Examples was produced as follows: Bacillus strains with count of $1.17 \times 10^{10}$ CFU/g. were combined with *Propionibacterium jensenii* strain P63 having count of $6.67 \times 10^9$ CFU g. and *Lactobacillus curvatus* having a count of at least $1.66 \times 10^9$ CFU/g. The water soluble carriers utilized were whey at approximately a 50% by weight content, maltodextrin M100 at approximately a 49% by weight content and balith at approximately 1% by weight content. The total count of all the bacteria was $2.0 \times 10^{10}$ CFU/g. These substances were mixed in a paddle blender for approximately 15 minutes. The novel composition was activated with the appropriate amount of warm water prior to use.

This invention works well on all types of commercial fowl, such as broilers or roasters, as well as geese, turkeys, ducks and the like. The invention also works at all various stages of poultry production such as brooder houses and grow houses.

EXAMPLE 1

The novel composition was applied to the surface of clean litter in each of four houses at four different contract farms of a broiler integrator in Virginia. At each site, an identical house was not treated and severed as the control. The description of the four sites and the amount of product applied is shown in Table 1.

TABLE 1

DESCRIPTION OF THE FOUR FIELD TRIAL SITES

| Site | Birds/house | Type of Litter | Product Applied per house (lb) |
|---|---|---|---|
| 1 | 36,500 | Hard wood chips | 2.25 |
| 2 | 31,000 | Peanut hulls | 2.0 |
| 3 | 31,000 | Pine shavings | 2.0 |
| 4 | 30,000 | Pine shavings | 1.90 |

The composition was applied at the recommended application rates (1 lb per 16,000 birds). The composition was dissolved in 15 gallons of water and sprayed over the entire surface of each treated house using a boom sprayer.

Birds were placed in the houses 24–48 hours after treatment of the litter. After 40–45 days, birds were shipped to the slaughter facility and samples of litter were collected from each of the four treated and untreated houses. The livability, feed conversion and gain per day were determined for all birds from the treated and untreated (control) houses at each of the four sites.

Litter samples taken at the start and end of the flock in both the control and treated houses at each site indicate the novel composition improved the microbiological quality of the litter. The mean total gram negative count of the litter at the end of the flock in the four treated houses was 62.9% lower than the mean total gram negative count of the litter in the four control houses. The mean total coliform count of the litter at the end of the flock in the four treated houses was 88.0% lower than the mean total coliform count of the litter in the four control houses.

The improvement in litter quality due to treatment with the novel composition lead to improvements in the growth and performance of the birds in the treated houses. The application of the novel composition improved livability of birds residing in treated houses by 15–96 points (1 point= 0.01%) for the four sites in this study (FIG. 1). Livability is the percentage of birds that lived from the time of placement in the house to the time of harvest. The mean livability for birds residing in treated houses was 56 points higher than the livability of the birds in untreated houses.

Figure 2:
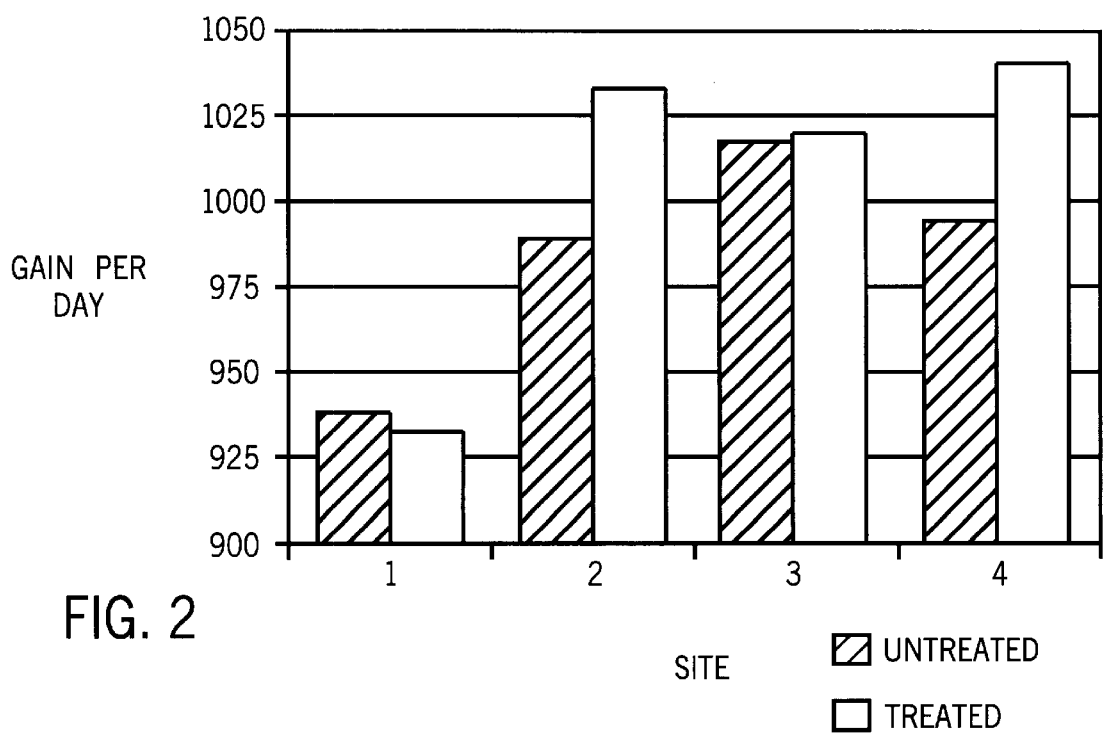
FIG. 2 illustrates improved weight gain of birds residing on litter treated with the novel composition.

The application of the novel composition improved birds gain per day in two of the four sites and had littler or no effect at the remaining two sites (FIG. 2). (Gain per day is the weight gain of the birds on a daily basis.) Where a difference was observed, the average improvement in gain per day for birds in treated houses was 4.6%. The figure used in Example 1 expresses this on a 1/10,000 pound basis.

Figure 3:
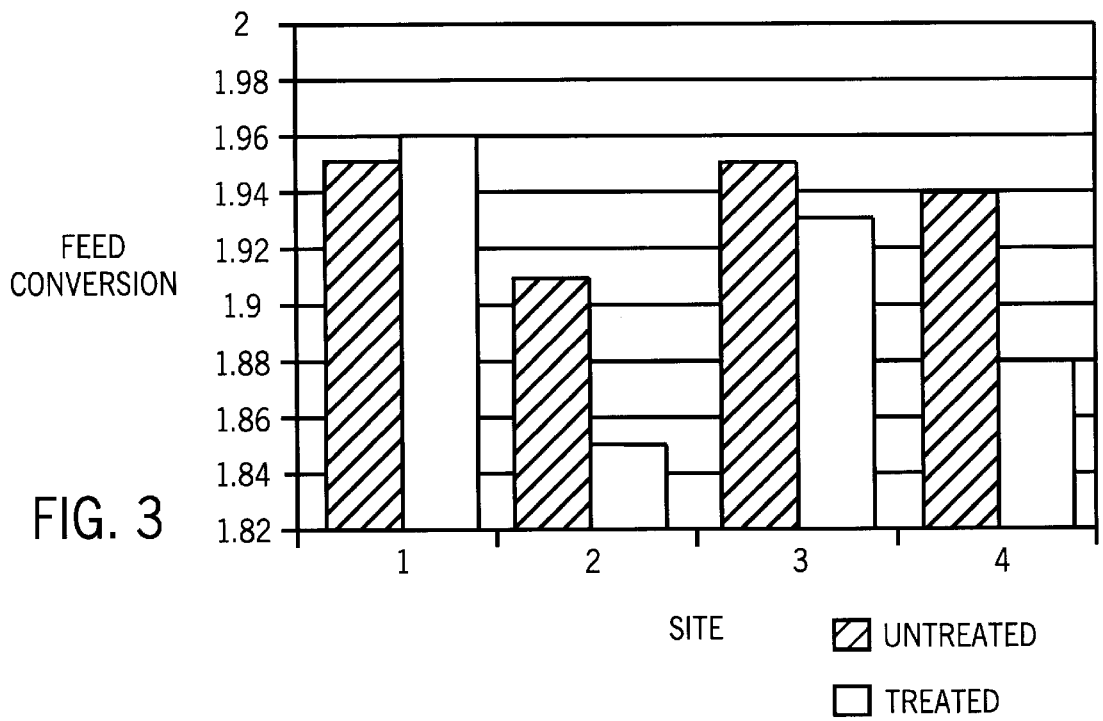
FIG. 3 illustrates the improved feed conversion of birds residing on litter treated with the novel composition.

Feed conversion was improved in three of the four sites by application of the novel composition (FIG. 3). Feed conversion is the amount of feed consumed per pound of weight gained and this is a measure of efficiency. The improvement in feed conversion ranged from 2 points for site 3 to 6 points each for sites 2 and 4.

Overall the novel composition improved the litter quality of all sites by reducing gram (−) and coliform bacteria in the litter. Concomitant with this improvement in litter quality was the improvement in the health and performance of the birds in the treated houses.

EXAMPLE 2

The novel composition was applied to freshly tilled litter in four houses (16,000 bird capacity) at the recommended application rates (See Tables 2–4). One pound of the composition was dissolved in 14 gallons of water and sprayed over the entire surface of each house using a boom sprayer. The application was repeated after each flock.

TABLE 2

COMPOSITION AMOUNT FOR CHICKENS

| Estimated bird finish weight | Composition Amount to use per 16,000 birds pounds |
|---|---|
| Broiler 4–5 LB | 1.0 |
| Roaster 7 LB | 1.5 |

TABLE 3

COMPOSITION FOR TURKEYS IN A TWO-STAGE PRODUCTION SYSTEM

| | Composition Amount to use per 3,00 birds | |
|---|---|---|
| Estimated bird finish weight | Brooder house pounds | Grow house pounds |
| up to 20 LB | 0.25 | 1.0 |
| 20–30 LB | 0.25 | 1.5 |
| 30–40 LB | 0.25 | 2.0 |

TABLE 4

COMPOSITION AMOUNT FOR TURKEYS IN A THREE-STAGE PRODUCTION SYSTEM

| | Composition Amount to use per 3,000 birds | | |
|---|---|---|---|
| Estimated bird finish weight | Brooder house pounds | Grow house pounds | Finish house pounds |
| up to 20 LB | 0.25 | 0.5 | 0.75 |
| 20–30 LB | 0.25 | 0.75 | 1.0 |
| 30–40 LB | 0.25 | 1.0 | 1.25 |

Birds (16,000 per house) were placed in the houses 24–48 hours after treatment of the litter. After 40–45 days, birds were shipped to the slaughter facility and samples of litter were collected from each treated house and four untreated houses.

The incidence of foot scabs and breast blisters were determined for all birds from four untreated (control) houses and the four treated houses for each flock at the time of slaughter.

Figure 4:
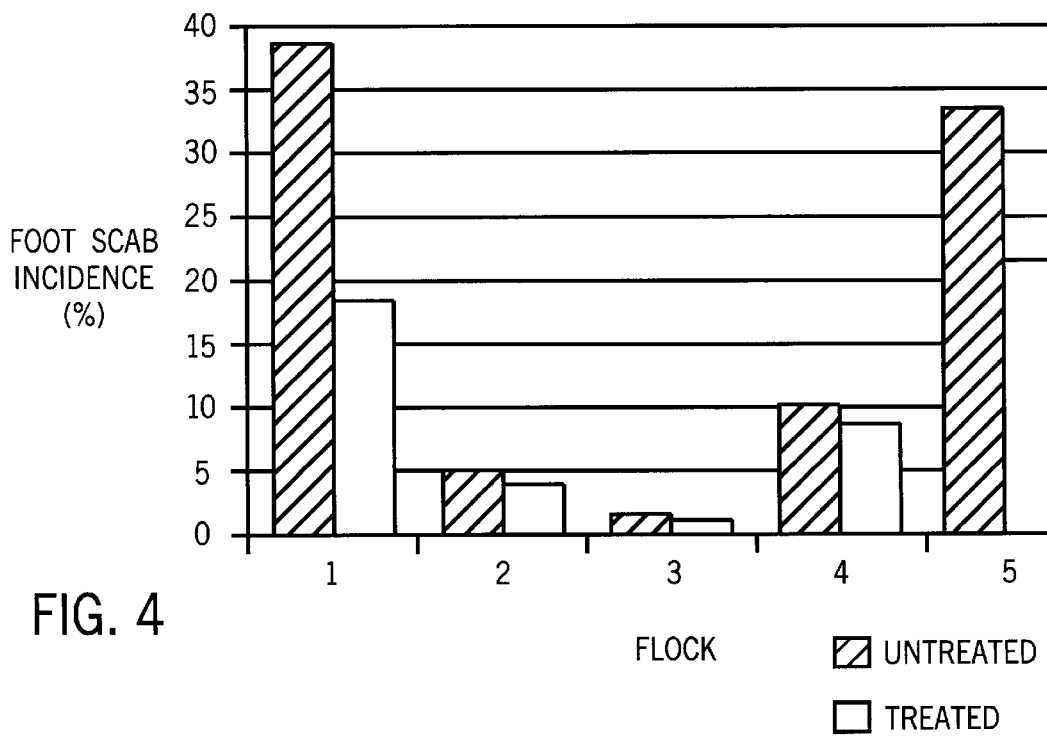
FIG. 4 illustrates the percentage of foot scab incidence between flocks treated with the invention versus those untreated.

The application of the novel composition reduced the incidence of foot scabs for bird residing in treated houses by 15–52% for the five flocks in this study (FIG. 4 and Table 5). The mean incidence of foot scabs for birds residing in treated houses was 31% lower than the incidence of foot scabs for birds in untreated houses.

TABLE 5

INCIDENCE OF BROILER FOOT SCABS IN UNTREATED AND TREATED HOUSES

| | Foot Scab Incidence (%)[1] | | |
|---|---|---|---|
| Flock (Slaughter Date) | Untreated Houses | Treated Houses | % Reduction of Foot Scabs |
| 1 (5/12) | 39.0 | 18.75 | 51.9 |
| 2 (7/20) | 5.0 | 4.22 | 15.6 |

TABLE 5-continued

INCIDENCE OF BROILER FOOT SCABS IN UNTREATED AND TREATED HOUSES

| | Foot Scab Incidence (%)[1] | | |
|---|---|---|---|
| Flock (Slaughter Date) | Untreated Houses | Treated Houses | % Reduction of Foot Scabs |
| 3 (9/20) | 1.75 | 1.25 | 28.6 |
| 4 (11/20) | 10.25 | 8.75 | 14.6 |
| 5 (2/1) | 33.5 | 21.6 | 35.5 |
| Mean (all flocks) | 17.9 | 10.9 | 39.1 |

[1]Mean foot scab incidence in four treated and four untreated houses for each flock. Each house contained 16,000 birds.

Overall, the incidence of foot scabs was dramatically affected by weather. As temperatures decreased in the fall and winter (flocks 1 and 5) the incidence of foot scabs dramatically increased. This was probably due to poor litter conditions associated with high humidity and cool temperatures. The incidence of foot scabs decreased in the spring and summer (flocks 2–4 was quite low) which is believed to be due to drier conditions in the houses during these periods. Treatment of litter with the novel composition reduced the incidence of foot scabs in all seasons. However, the reduction in the incidence of foot scabs was greatest during periods of the highest incidence. From this data it appears that the application of the novel treatment composition helped to prevent the expected increase in the incidence of foot scabs during cooler temperatures.

Figure 5:
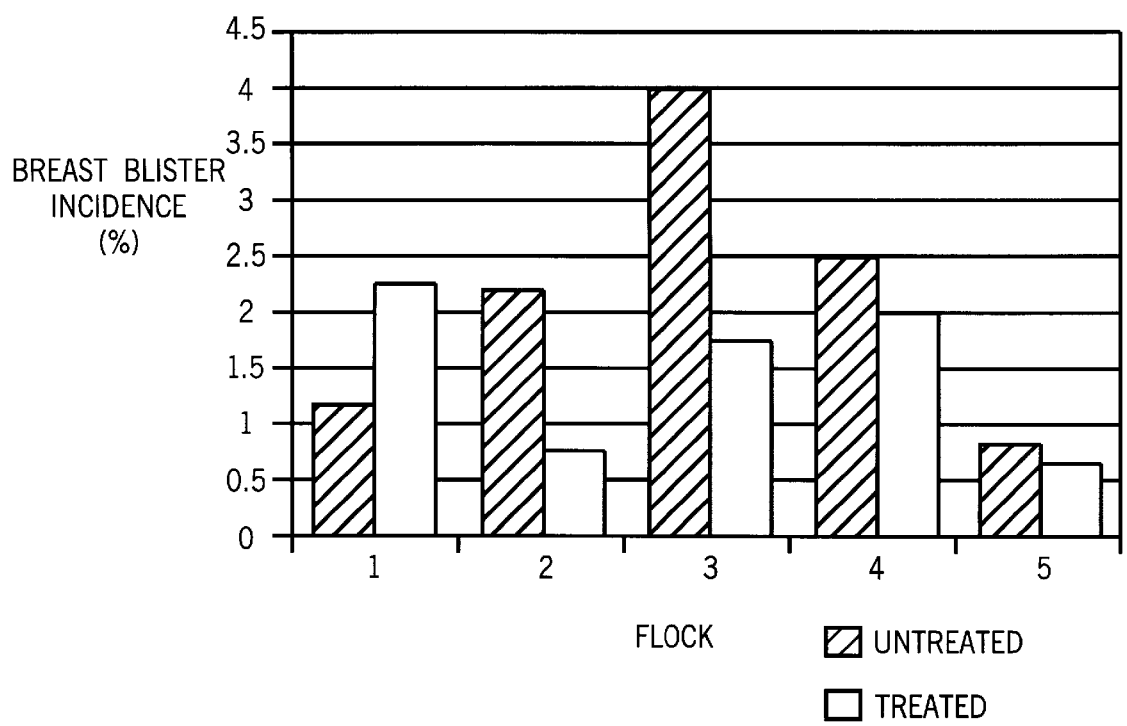
FIG. 5 illustrates the percent of breast blister incidence between flocks treated with invention versus those untreated.

The incidence of breast blisters was also monitored. The incidence of breast blisters for birds residing in houses treated with the novel treatment composition decreased in four of the five flocks in this study (FIG. 5 and Table 6). In the four flocks where a reduction in breast blisters was observed, the reduction in blisters ranged from 20–66% compared to the incidence of breast blisters for birds residing in control houses. The mean reduction of breast blisters over all five flocks was 30.8%. It is not known why the incidence of breast blisters increased in the first treated flock and appears to be an aberration. The incidence of breast blisters also appeared to vary seasonally. The incidence increased as temperatures increased in the spring and summer. This was probably due to the birds spending more time laying on the litter to dissipate heat.

TABLE 6

INCIDENCE OF BROILER BREAST BLISTERS IN UNTREATED AND TREATED HOUSES

| | Breast Blister Incidence (%)[1] | | |
|---|---|---|---|
| Flock (Slaughter Date) | Untreated Houses | Treated Houses | % Reduction of Breast Blisters |
| 1 (5/12) | 1.16 | 2.25 | — |
| 2 (7/20) | 2.20 | 0.75 | 65.9 |
| 3 (9/20) | 4.00 | 1.75 | 56.3 |
| 4 (11/20) | 2.50 | 2.00 | 20.0 |
| 5 (2/1) | 0.83 | .66 | 20.5 |
| Mean (all flocks) | 2.14 | 1.48 | 30.8 |

[1]Mean breast blister incidence in four treated and four untreated houses for each flock. Each house contained 16,000 birds.

Based on the results for the five flocks (640,000 birds) monitored in this study, the novel treatment composition reduced the incidence of foot scabs by 39.1%, reduced the incidence of breast blisters by 30.8% and did not increase air sac infections.

The application rate of the invention is dependent upon the expected waste production which is in turn based on the type of bird and market weight. See Tables 2–4.

The bacteria spores and cells must be freeze dried during processing to preserve their activity. The freeze dried bacteria present in this invention must be rehydrated prior to use. The specified amount as seen in Tables 2–4 is mixed with water in a clean container or directly to the applicator tank. After approximately 5–15 minutes, the mixture is thoroughly dissolved and the bacteria have been rehydrated. The volume of water must be enough to effectively disperse the product over the entire surface to be treated. The solution must be applied by spraying it directly onto the surface of the freshly tilled or new litter. The initial application of the novel composition should be to new litter after complete clean-out and repeated before the placement of each successive flock. The novel composition must not be applied more than 48 hours before the bird will be placed in the house.

When part room brooding is used, the invention should be applied to each section separately no more than 48 hours before the birds are allowed into that section. To insure maximum activity, use the solution as soon as possible after hydration. Certain factors such as temperature and water purity may cause the solution to deteriorate if left standing for extended periods of time. The solution should be used within 8 hours after hydrating.

I claim:

1. A biological poultry litter treatment composition comprising:
   a bacteriocin-producing bacteria, said bacteriocin-producing bacteria comprising *Propionibacterium jensenii*;
   a protease-producing bacteria, said protease-producing bacteria is of the genus Bacillus and is selected from the group consisting of *Bacillus subtilis, Bacillus licheniformis* and *Bacillus amyloliquefaciens*;
   a starch fermenting bacteria, said starch fermenting bacteria comprises *Lactobacillus curvatus*; and
   a carrier.

2. The composition of claim 1 wherein said protease-producing bacteria produces proteolytic enzymes selected from the group consisting of neutral proteases, alkaline proteases, and a combination thereof.

3. The composition of claim 1 wherein said *Propionibacterium jensenii* is strain P63.

4. The composition of claim 3 wherein said P63 has an activity of at least approximately $6.67 \times 10^{10}$ CFU/g.

5. The composition of claim 1 wherein said carrier is a water soluble carrier.

6. The composition of claim 5 wherein said composition further contains a moisture binding agent and said water soluble carrier is selected from the group consisting of whey, maltodextrin, and a mixture thereof.

7. The composition of claim 6 wherein said moisture binding agent is balith.

8. The composition of claim 7 wherein said whey is present at approximately 50% by weight, maltodextrin is present at approximately 49% by weight and said balith is present at approximately 1% by weight.

9. The composition of claim 6 wherein said water soluble carrier consists of approximately 50% by weight maltodextrin and approximately 50% by weight whey.

10. The composition of claim 6 wherein said maltodextrin is present in a range of approximately 40%–60% by weight and said whey is present in a range of approximately 40%–60% by weight.

11. The composition of claim 1 wherein said *Lactobacillus curvatus* has an activity of at least $1.66 \times 10^{10}$ CFU/g.

12. The composition of claim 1 wherein said Bacillus bacteria has an activity of at least approximately $1.17 \times 10^{10}$ CFU/g.

13. The composition of claim 1 wherein said Bacillus are present in a ratio of *Bacillus subtilis* at 10%, *Bacillus licheniformis* at 20% and *Bacillus amyloliquefaciens* at 70%.

14. The composition of claim 1 wherein said Bacillus are present in the following ranges: *Bacillus subtilis* at approximately 5–15%; *Bacillus licheniformis* at approximately 15–25%; and *Bacillus amyloliquefaciens* at approximately 65–75%.

15. The composition of claim 1 wherein said composition further includes spores and vegetative cells.

16. A method for reducing the ammonia concentration and lower pH in poultry litter comprising:
    combining a bacteriocin-producing bacteria, said bacteriocin-producing bacteria comprising *Propionibacterium jensenii*;
    a protease-producing bacteria, said protease-producing bacteria is of the genus Bacillus and is selected from the group consisting of *Bacillus subtilis, Bacillus licheniformis* and *Bacillus amyloliquefaciens*;
    a starch fermenting bacteria, said starch fermenting bacteria comprises *Lactobacillus curvatus* to form a mixture; and
    applying said mixture onto poultry litter.

17. The method of claim 16 wherein said mixture further contains a carrier.

18. The method of claim 17 wherein said carrier is water soluble and said mixture is dissolved in water prior to applying said mixture onto said poultry litter.

19. The method of claim 16 wherein said protease-producing bacteria produces proteolytic enzymes selected from the group consisting of neutral proteases, alkaline proteases, and a combination thereof.

20. The method of claim 16 wherein said *Propionibacterium jensenii* is strain P63.

21. The method of claim 20 wherein the activity of P63 is at least $6.67 \times 10^{10}$ CFU/g.

22. The method of claim 16 wherein the activity of said Bacillus bacteria is at least $1.17 \times 10^{10}$ CFU/g.

23. The method of claim 16 wherein the activity of *Lactobacillus curvatus* is at least $1.66 \times 10^{9}$ CFR/g.

24. The method of claim 16 wherein said mixture further contains a moisture binding agent and a water soluble carrier selected from the group consisting of maltodextrin, whey, and a combination thereof.

25. The method of claim 24 wherein said moisture binding agent is balith.

* * * * *